United States Patent
Kantor et al.

(10) Patent No.: US 7,361,303 B2
(45) Date of Patent: Apr. 22, 2008

(54) MEDICAL WASTE TREATMENT UNIT

(75) Inventors: Steven L. Kantor, Oshawa (CA); Michael Griffin, Toronto (CA); Roman Ruginets, Thornhill (CA); Douglas Norton, Whitby (CA)

(73) Assignee: Environmental Waste International Inc., Ajax (CA)

( * ) Notice: Subject to any disclaimer, the term of this patent is extended or adjusted under 35 U.S.C. 154(b) by 145 days.

(21) Appl. No.: 10/381,186

(22) PCT Filed: Sep. 21, 2001

(86) PCT No.: PCT/CA01/01346

§ 371 (c)(1),
(2), (4) Date: Aug. 19, 2003

(87) PCT Pub. No.: WO02/24354

PCT Pub. Date: Mar. 28, 2002

(65) Prior Publication Data

US 2004/0054240 A1    Mar. 18, 2004

(30) Foreign Application Priority Data

Sep. 22, 2000  (CA) .................................. 2320455

(51) Int. Cl.
*B61L 2/00* (2006.01)
*B01J 19/08* (2006.01)
*B09B 3/00* (2006.01)

(52) U.S. Cl. ............... 422/22; 422/184.1; 422/186.04; 219/678; 219/690; 219/702; 219/708

(58) Field of Classification Search ............ 422/21, 422/184.1, 186.04; 219/678, 690, 702, 708
See application file for complete search history.

(56) References Cited

U.S. PATENT DOCUMENTS

| | | | | |
|---|---|---|---|---|
| 4,104,205 A | * | 8/1978 | Novotny et al. | 526/339 |
| 4,228,135 A | | 10/1980 | Wolff | 422/296 |
| 4,930,442 A | | 6/1990 | Iida et al. | 118/723 |
| 5,322,603 A | * | 6/1994 | Kameda et al. | 204/158.2 |
| 5,393,500 A | * | 2/1995 | Kameda et al. | 422/186 |
| 5,429,799 A | * | 7/1995 | Shieh et al. | 422/21 |
| 5,507,927 A | * | 4/1996 | Emery | 204/157.43 |
| 5,877,395 A | * | 3/1999 | Emery | 422/186 |
| 5,951,947 A | * | 9/1999 | Hunt | 422/21 |
| 6,097,015 A | * | 8/2000 | McCullough et al. | 219/686 |
| 6,133,500 A | * | 10/2000 | Emery | 422/186 |
| 6,248,985 B1 | * | 6/2001 | Tomasello | 219/679 |
| 6,262,405 B1 | * | 7/2001 | Wicks et al. | 219/679 |
| 6,344,638 B1 | * | 2/2002 | Tomasello | 219/770 |
| 6,524,539 B1 | * | 2/2003 | Katschnig et al. | 422/186.07 |
| 6,537,493 B1 | * | 3/2003 | Mednikov | 422/21 |

(Continued)

FOREIGN PATENT DOCUMENTS

DE    3627367 C1    12/1987

(Continued)

*Primary Examiner*—N. Bhat
(74) *Attorney, Agent, or Firm*—Dimock Stratton LLP (57) ABSTRACT

A method and apparatus for reducing organic waste. The apparatus comprises a conveyor to move waste to a first chamber for weighing waste and purging oxygen, a second chamber for treating, sterilizing and reducing waste by reverse polymerization, and a third chamber for cooling reduced and sterilized waste.

40 Claims, 10 Drawing Sheets

U.S. PATENT DOCUMENTS

2002/0068011 A1 * 6/2002 Kongmark .................. 422/21

FOREIGN PATENT DOCUMENTS

| EP | 0441923 A1 | 2/1991 |
| EP | 0555171 A2 | 8/1993 |
| EP | 0908189 A2 | 4/1999 |
| EP | 1114679 A1 | 7/2001 |
| GB | 827760 | 2/1960 |
| WO | WO 91/15247 | 10/1991 |
| WO | WO 99/51366 | 10/1999 |

* cited by examiner

FIG. 9

MEDICAL WASTE TREATMENT UNIT

FIELD OF THE INVENTION

This application is a 371 of PCT/CA01/01346, filed Sep. 21, 2001.

This invention relates to a process and apparatus for the reduction of organic waste materials by reverse polymerization.

BACKGROUND OF THE INVENTION

There has long been and continues to be a very significant need for effective means of destroying, sterilizing or otherwise neutralizing waste from a variety of industrial or institutional sources. In many instances, it is impractical or undesirable to move these waste materials off-site for treatment. At the same time, the only on-site treatment which is economically viable has been by way of burning.

As has become more evident in recent years, a wide variety of toxic gases are frequently given off in burning of industrial or institutional waste, such as hospital waste.

Medical and biomedical waste accounts for up to 50% of all waste material generated by hospitals. This includes anatomical waste, animal waste, laboratory waste, human blood and body fluid, and waste sharps, as well as any waste which may have come in contact with infectious agents at any level of exposure.

Current methods of treating hospital waste, such as incineration or steam autoclaving result in not only toxic gases but also in an incomplete or uneven sterilization of the waste, thus requiring further treatment steps at great time and expense. In addition, standard incinerators or autoclaves require expensive pollution control equipment to remove potentially toxic emissions from the process. In all, the volume reduction from each of these alternatives fails to meet the costs and environmental hazards inherent in the processes.

While microwave treatment has been proposed as a method of dealing with such waste, systems have not become widely available which are secure against leakage, environmentally acceptable and economically reasonable. For example, the systems must be sealed against leakage at all steps of the process to prevent not only against leaking of toxic gases but also of microwaves. The systems must also be cost and energy efficient. Thus it is necessary to apply an appropriate amount of microwave energy, for a suitable time period, for the amount of waste being treated.

PRIOR ART

Reference may be had to U.S. Pat. No. 5,322,603, issued Jun. 21, 1994 to Kameda et al., "Method of an Apparatus for Treating Infectious Medical Wastes" as an example of the use of microwaves in the reduction of medical waste. However, that reference uses the microwaves in a pre-treatment step to heat the waste and evaporate the water from the waste.

Reference may also be had to U.S. Pat. No. 5,877,395A, issued Mar. 2, 1999 to Emery, "Method and apparatus for the controlled reduction of organic material" as a further example of the use of microwaves in the reduction of organic materials. However, that reference does not enclose phases of the process in different chambers, nor purge the loading chamber as part of the process.

Applicant is also aware of the following prior art references related to the use of microwaves in the reduction of organic materials. However, none of the references listed below solves the problems inherent to the reduction of medical or biomedical waste in the manner as described in the present invention:

U.S. Pat. No. 4,937,411 of Suzuki et al., issued Jun. 26, 1990;
U.S. Pat. No. 5,425,316 of Malone, Issued Jun. 20, 1995;
U.S. Pat. No. 5,521,360 of Johnson et al., issued May 28, 1996;
Canadian Application Serial No. 2,080,349 of ABB Sanitec, published Oct. 14, 1991;
Canadian Application Serial No. 2,051,445 of ABB Environmental Services, published Oct. 20, 1990;
Canadian Application Serial No. 2,079,332 of IIT Research Institute, published Oct. 1, 1991;
Canadian Application Serial No. 2,153,808 of Holland, published Aug. 18, 1994;
Canadian Application Serial No. 2,087,526 of Holland, published Jan. 28, 1992; and
Canadian Application Serial No. 2,026,103 of Roszel, published Mar. 26, 1992.

SUMMARY OF THE INVENTION

It is thus an object of the present invention to provide a complete process and apparatus for the reduction of organic waste.

In one aspect of the invention, there is provided a process for the reduction of organic waste in an apparatus which comprises a first chamber, a second chamber and a third chamber. The process comprises the steps of loading the waste into the first chamber, weighing the waste and purging the first chamber of oxygen. Thereafter, the process involves transferring the waste to the second chamber and treating, sterilizing and reducing the waste in a non-pyrolytic process for a first period of time by means of depolymerization. Thereafter, the process involves transferring the reduced and sterilized waste to the third chamber, cooling the reduced waste for a second period of time and grinding the reduced waste for storage and ultimate disposal.

In another aspect of the invention, the depolymerization is carried out by means of the application of microwave energy in an oxygen free atmosphere.

In another aspect of the invention, the pressure in the first, second and third chambers is balanced such that the pressure in the first and third chambers are maintained at a higher level than the pressure in the second chamber.

In another aspect of the invention, there is provided an apparatus for the reduction of organic waste in which the apparatus comprises a conveyor to move the waste within the apparatus. There is also provided a first chamber comprising weighing means to determine a weight of the waste and purging means to purge the apparatus of oxygen. A second chamber comprises reduction means to treat, sterilize and reduce the waste for a first period of time and a third chamber comprises cooling means to cool the reduced and sterilized waste for a second period of time. There is also provided sealing means to seal each of the first, second and third chambers from the other chambers and from exterior of the apparatus when in use.

In another aspect of the invention, the third chamber further comprises grinding means to comminute the reduced waste for storage and ultimate disposal.

In yet another aspect of the invention, the sealing means comprises a shutter assembly moveable between an open position and a partially closed position and between the partially closed position and a closed position.

In still another aspect of the invention, the shutter assembly comprises a door and a door frame, with the door suspended on the door frame. There is also provided drive means to move the door vertically between the open position and the partially closed position and a cylinder assembly for moving the door horizontally between the partially closed position and the closed position. The drive means may comprise a pneumatic cylinder or an electric motor.

In another aspect of the invention, there is provided a scrubber system designed to remove hydrogen chloride and hydrochloric acid from the gas stream generated from the treated waste.

In another aspect of the invention, there is provided a means for further removing hydrocarbon gases from the apparatus, after the scrubber system. That means comprises a thermal oxidizer or a turbine.

In another aspect of the invention, there is provided a power supply to power the magnetrons.

In another aspect of the invention, there is provided a microwave delivery apparatus for the delivery of the microwaves from the magnetron to the medical waste reduction apparatus.

In another aspect of the invention, the microwave delivery apparatus comprises a magnetron mounted on and with its anode projecting into a waveguide, means for isolating the magnetron from the second chamber, and tuning means in the waveguide for optimizing coupling of the magnetron to the chamber.

BRIEF DESCRIPTION OF THE DRAWINGS

These and other advantages of the invention will become apparent upon reading the following detailed description and upon referring to the drawings in which:—

While the invention will be described in conjunction with illustrated embodiments, it will be understood that it is not intended to limit the invention to such embodiments. On the contrary, it is intended to cover all alternatives, modifications and equivalents as may be included with in the scope of the invention as defined by the appended claims.

DETAILED DESCRIPTION OF THE PREFERRED EMBODIMENTS

The medical waste reduction system and apparatus 2 of the present invention is preferably divided into four main sections, material handling, microwave generation, nitrogen generation, and environmental control. These sections are all linked together through a distributed control system that coordinates the functions of all components to ensure the safe and efficient treatment of medical and biomedical waste. The medical waste reduction system uses the depolymerization process to sterilize any infectious material.

Depolymerization refers to the reduction of organic material, such as medical or biomedical waste through the application of microwave energy in an oxygen free atmosphere. Microwave energy is absorbed by the organic material, causing an increase in molecular vibration and straining inter-molecular bonds, leading to the generation of narrow band infrared energy. Narrow band infrared energy is re-adsorbed by surrounding material, increasing the amount of energy in the bonds until the bonds break. The breaking of the bonds results in the conversion of complex organic compounds into simpler compounds of lower molecular weight. Depolymerization is alternately referred to as reverse polymerization. Depolymerization is much faster than pyrolysis and the conversion from long chain polymers to shorter chain molecules is more extensive.

Figure 1:
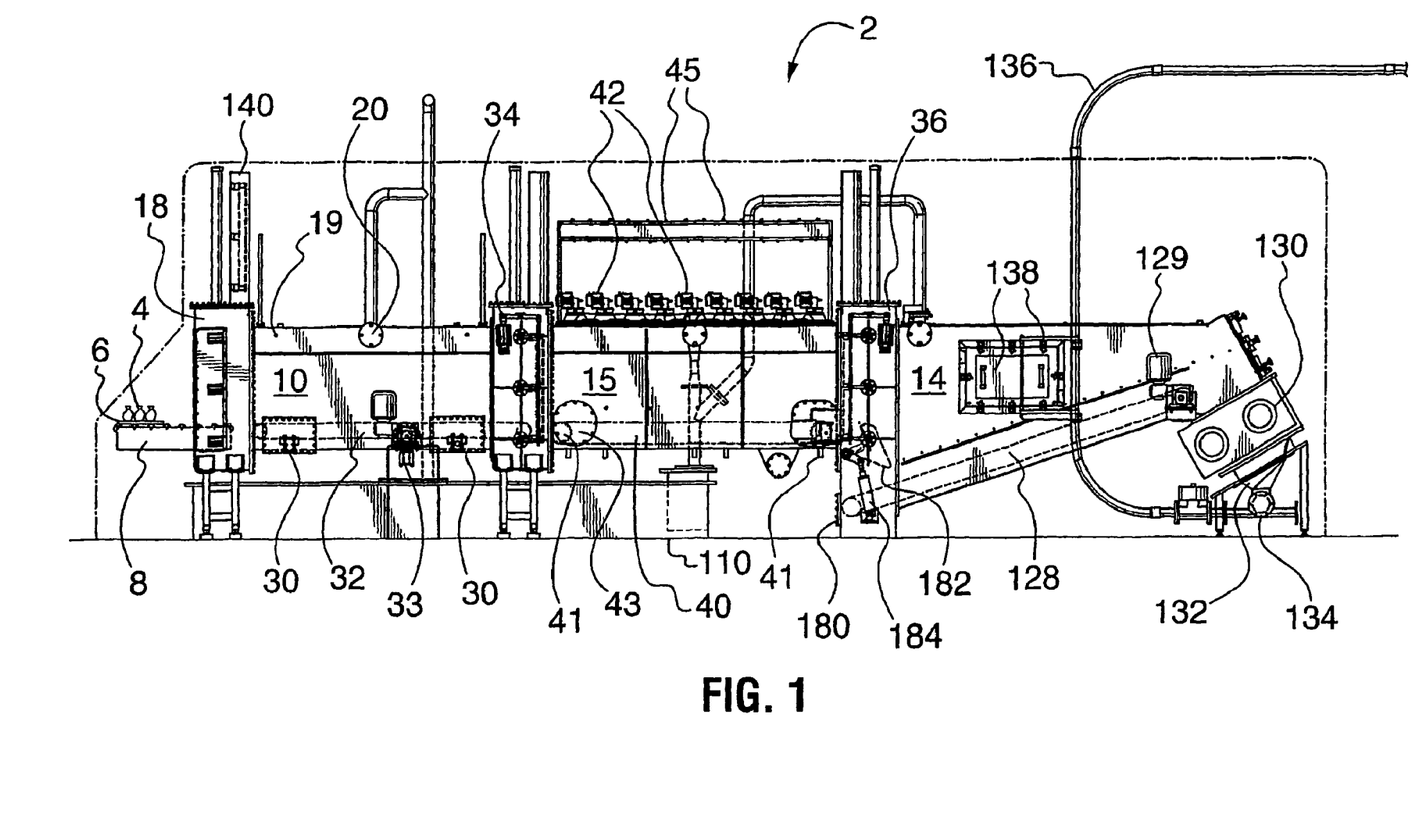
FIG. 1 is a side elevation plan view of the apparatus of the present invention, with cosmetic covers removed therefrom.
Figure 1A:
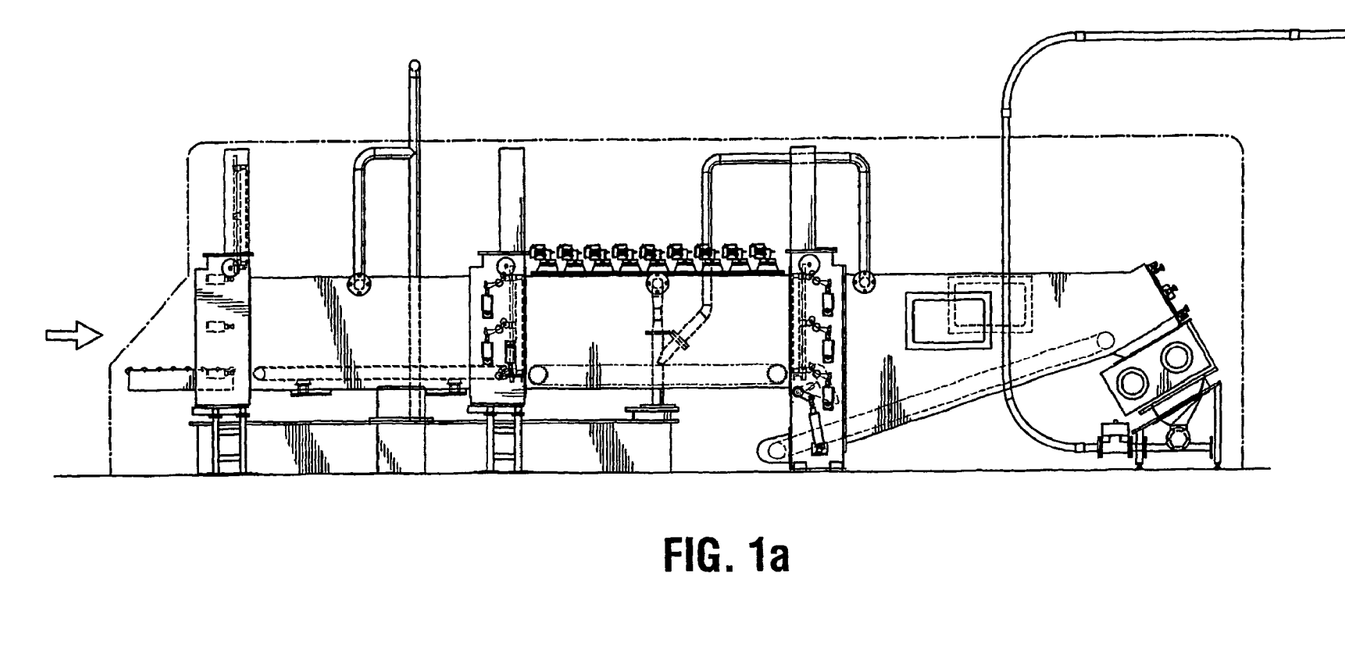
FIG. 1*a* is a side elevation plan view of an alternate embodiment of the apparatus of the present invention, with cosmetic covers removed therefrom.
Figure 2:
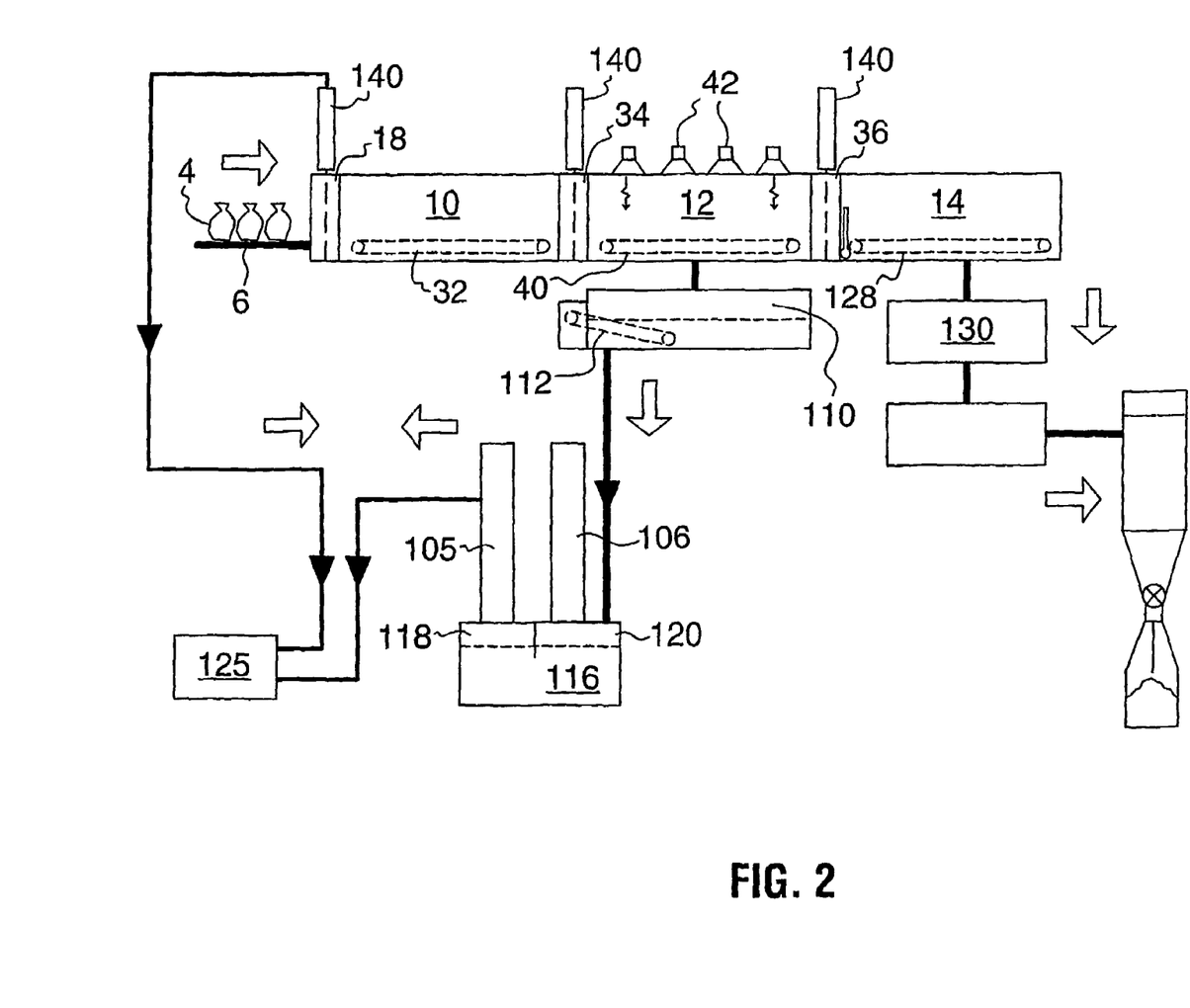
FIG. 2 is a schematic overview diagram of the process of the present invention.

Medical and biomedical waste 4 is collected and delivered to the medical waste reduction apparatus 2. The waste 4 can be collected in either bags or boxes. Once the waste has been collected it is placed in a cardboard tray 6 and placed on the inlet conveyor 8 for the treatment system.

The entire reduction process has three essential steps, carried out in three distinct chambers of the apparatus 2. The first chamber 10 is the weighing and purging chamber. The second chamber 12 is the reduction chamber and the third chamber 14 is the cooling and grinding or discharge chamber.

The cardboard tray 6 allows the waste 4, in either bags or boxes, to be transferred to the apparatus 2. The tray 6 will act to hold any potential leakage from the bags or boxes. The tray 6 will further act like a non-stick coating so that the carbonized material falls off the conveyor without sticking. If there were no cardboard tray, or other suitable carrying means for the waste, the carbonized material would have the tendency to fall through and stick to the conveyor, particularly in the reduction chamber 12.

Another advantage of the cardboard tray 6 as a carrying means is that it holds its shape even when subjected to the carbonization process, without interfering with the efficacy of the process, thus allowing the waste to transferred from the reduction chamber 12 to the discharge chamber 14.

A first shutter assembly 18, acting as a door between the first chamber 10 and the environment, is opened and the tray 6 containing the waste 4 to be treated is loaded into the weighing and purging chamber 10. Safety interlocks are in place at this point to ensure that the closing shutter door assembly 18 cannot harm the operator.

Once the waste 4 has been completely loaded into the weighing and purging chamber 10 the first shutter door assembly 18 is closed and sealed. The operation of the reduction apparatus 2 is completely automatic from this point.

Nitrogen gas ($N_2$) is fed to the weighing and purging chamber 10 through an inlet pipe 19, displacing oxygen from the chamber 10 to prevent any oxidation of the waste from occurring in the reduction chamber 12. The gas outlet 20 from the weighing and purging chamber 10 is vented through the scrubber (described in more detail below).

Nitrogen gas is used to displace oxygen in the depolymerization process. The nitrogen gas is preferably supplied by a Pressure Swing Absorption ("PSA") generator (not shown) that provides nitrogen at approximately 99.5% purity. Currently a BOC brand PSA generator is used to supply the nitrogen purge gas. There are other nitrogen generation systems available using different technologies.

If nitrogen pressure is lost the reduction system will automatically shut down in a safe and orderly manner. The nitrogen generator includes a surge tank (not shown) which provides an emergency supply of nitrogen, if required.

Load cells 30 are located about the conveyor 32 in the weighing and purging chamber 10 to record the mass of the waste load 4, which reading is fed to the control system. There are preferably four load cells 30, one on each side of the conveyor, at the beginning and end of the flow path within the first chamber 10. The mass is recorded and used to determine the length of treatment cycle required for sterilization and carbonization. The load is moved through the chamber 10 by the conveyor 32, driven by motor 33 in the conventional fashion.

Once the weighing and purging cycle is complete a second shutter door assembly 34 opens and the waste 4 is transferred from the weighing and purging chamber 10 to the second chamber, the reduction chamber 12. The reduction chamber 12 is used to treat, sterilize and reduce the waste using the reverse polymerization process described above.

After the waste 4 has been transferred to the reduction chamber 12 the second shutter door assembly 34 is closed and clamped. A third shutter door assembly 36, between the second chamber 12 and the third chamber 14 is also closed and clamped to seal the reduction chamber 12, thereby isolating the reduction chamber 12 from the remaining part of the apparatus 2.

The pressures in the three different chambers are balanced; the pressure in the weighing and purging chamber 10 and in the cooling/grinding chamber 14 is maintained at a slightly higher pressure than the pressure in the reduction chamber 12. This is to ensure that any minor leakage through the second 34 and third 36 shutter door assemblies will result in flow of nitrogen into the reduction chamber 12 and inhibit the reverse flow of process gas.

The second chamber 12 houses a conveyor 40 and a number of magnetron assemblies 42. The drive means 41 for the conveyor 40 is accessible to the operator by means of access ports 43.

The number of magnetron assemblies 42 will depend on the overall size and purpose of the apparatus 2. It is anticipated that for a typical medical waste application, approximately 14 assemblies 42 will be sufficient, although more or less could be utilized. Each assembly is preferably equipped with a corresponding filament transformer 45 housed at the top of the chamber 12.

Figure 4:
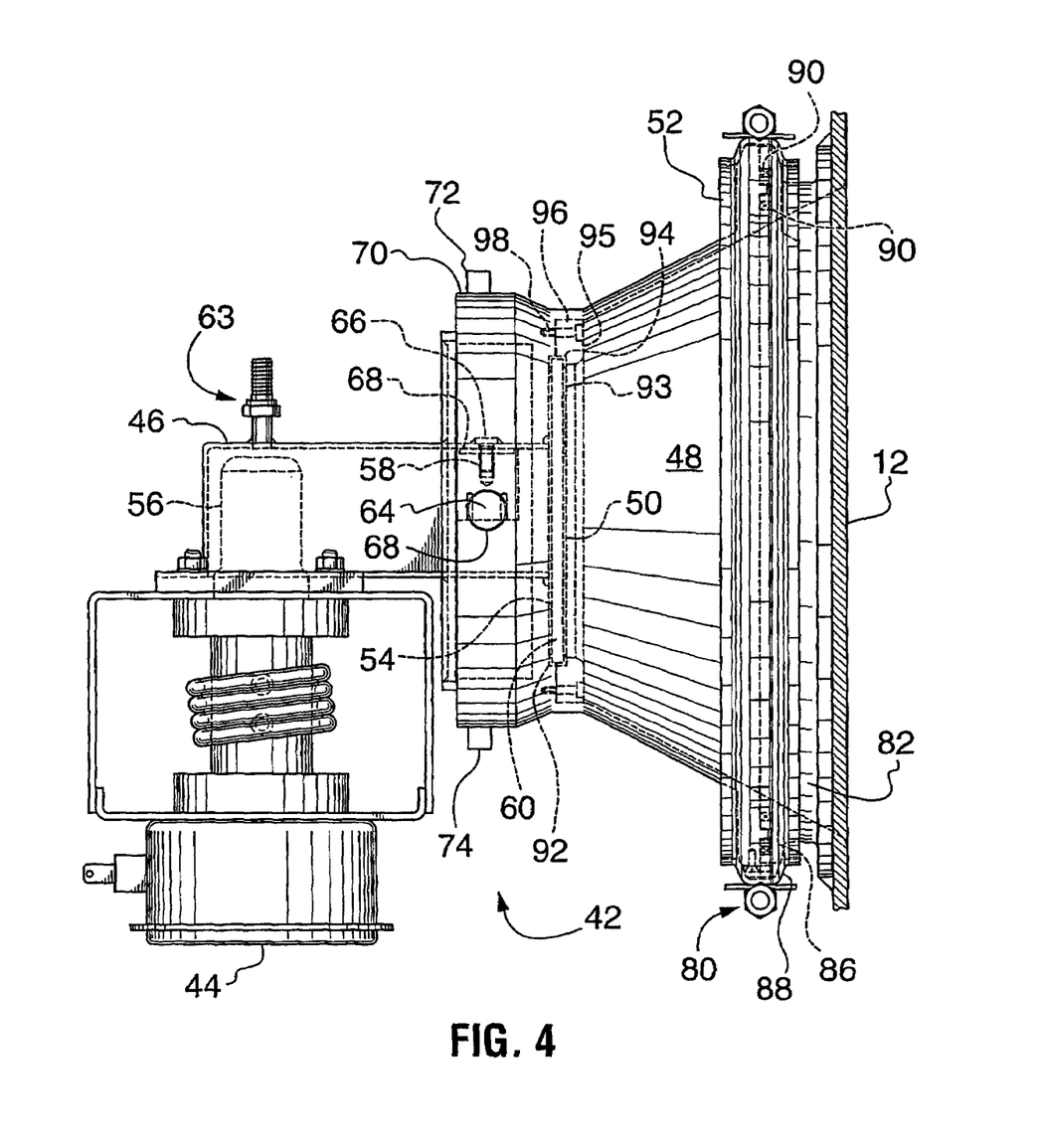
FIG. 4 is a plan view, partly in section and partly cutaway of the microwave delivery apparatus for use in the apparatus of the present invention.

As best seen in FIG. 4, the design of the assembly 42 is unique in that the magnetron 44 is mounted on the side of a short rectangular waveguide 46 and there is a flared end part, shown as a truncated cone 48 mounted to an end 50 of the waveguide 46. The base 52 of the cone 48 is at or near the top of the second chamber 12 thereby directing the microwaves into the chamber 12 in a space efficient manner.

The assembly 42 further preferably comprises a barrier means 54 between the anode 56 of the magnetron 44 and the chamber 12, and tuning means 58 in the waveguide 46 for optimizing coupling of the magnetron 44 to the chamber 12.

The barrier means 54 is preferably a substantially microwave transparent and porous round plate 60 mounted adjacent an end of the waveguide 46, preferably adjacent the end 50 of the waveguide 46 which is adjacent the second chamber 12. The material for the plate 60 is chosen so as to minimize absorption of microwaves but so as to provide maximum protection for the anode 56 from vapor and flying solid residue. The plate 60 also provides thermal shock resistance within the waveguide 46. It has been found that a ceramic alumina plate, or one made of porous TEFLON™, will adequately function as the barrier means. The thickness of the plate 60 may also change the characteristics of the plate 60 and therefore, must be taken into consideration in choosing the material. A typical plate thickness may be about 4 mm.

The preferred porosity of the plate 60 is approximately 32%. A typical, although, not exclusive composition of the plate 60 is as follows:

| | |
|---|---|
| $Al_2O_3$: | 99.07% |
| $SiO_2$: | 0.43% |
| MgO: | 0.20% |
| CaO: | 0.22% |
| $Na_2O$: | 0.04% |
| $K_2O$: | trace |
| $Fe_2O_3$: | 0.05% |
| $TiO_2$: | trace |

To keep the plate clean, in particular to maintain the exposed face of the plate 60 on the chamber side clean of gases or solid particles which would deposit on it otherwise, there is preferably provided a nitrogen gas purge at 63 through the plate 60 into the reduction chamber 12, with the magnetrons 44 powered on. The amount of nitrogen gas flow, as well as the pressure at which it is supplied, is controlled to achieve the cleaning purpose. The Nitrogen gas purge also assists in keeping the plate cool, so as to avoid an unwanted build-up of heat in the waveguide 46.

The tuning means 58 is preferably a tuner 64, which may be preset or adjustable, and in one preferred case composes an adjustable screw 66 projecting into the waveguide 46. A tuning disc 68 may be fixed to the end of the tuning screw. It is generally desired to have resonance in the waveguide 46 and therefore, the optimum position of the tuner 64 (as a special resonant adjustment) is where there is minimum reflection back through the porous plate 60.

Thus, the variables in setting the tuner 62 include the thickness of the plate 60 the plate/tuner/anode distance and the weight of the load to be processed. It is preferable to have a controlled uniform temperature within the waveguide 46 so as to protect the anode 56 and avoid the possibility of arcing. Thus, there may be provided a water jacket 70 disposed around the waveguide 46, preferably proximate to or integral with the end 50 of the waveguide 46 near the cone 48 to cool the waveguide 46. The jacket 70 is preferably provided with inlet 72 and outlet 74 disposed at opposite sides thereof and connected to a source of water (not shown).

The cone 48 may be connected to the chamber 12 by means of a connector assembly 80. In one embodiment the connector assembly 80 comprises a base ring 82 welded to the top of the reduction chamber 12, and a first clamping flange 84 integral with the base ring 82. A second clamping flange 86 integral with the cone 48 is releasably clampable to the first clamping flange 84 by suitable means, such as a clamp ring 88 and screw tighteners. Sealing rings 90 between the mating flanges 84, 86 may also be used.

The plate 60 can be seated within the elastomeric "U" shaped endless housing or ring 92. This ring 92 snaps on the outer edge 93 of the plate 60 and is preferably made of high temperature unfilled silicone. The ring 92 provides a soft cushion at the window mount and seals the plate 60 at its perimeter 94. Thus, the nitrogen flow is directed outwardly through the plate 60 at its porous surface while its perimeter 54 is sealed. In this manner, the nitrogen flow is directed towards the desired direction without having to supply excess nitrogen to account for additional leakage at the outer edge of the plate 60.

At the top 95 of the cone 48 there is provided a clamping ring 96 secured by bolts 98 onto the top 95 of the cone 48 to hold the plate 60 and ring 92 in place.

The magnetrons 44 are powered and the reduction cycle is started. The length of the reduction cycle is determined by the mass of waste that has been loaded into the system, and by the time to reach 100_C. All of the operating conditions are monitored by the control system to ensure that the waste is treated properly.

The monitored functions include microwave power, chamber pressure and temperature. Each magnetron 44 is individually monitored and can be independently adjusted or shut down if abnormal operation is detected. The length of the reduction cycle, and the power level of the magnetrons is adjusted based on the information collected by the control system.

The magnetron based microwave-generating system using high-voltage full-wave rectifier as a power supply, represents a very specific non-linear, low impedance load. The thyristor (triac) control has been designed to provide high quality and stable control of magnetron output power. This designed circuit can be able to provide the power control from low minimum as 60-70 watts of microwave power output with stabilization ±0.5%. The output maximum is limited by supply line voltage only (as 98% from the line voltage value). The power stabilization as ±0.5% is linear function and not depended from current output power or supply line voltage.

In addition, there are some preferable features which together give full control of the magnetron power operation. A total combination of all those features significantly increases a lifetime of magnetron's anode and filament; high-voltage PS components such as a HV Transformer, HV Capacitors, and HV Diodes, and makes this power supply very unique. The microwave operation cost may be also sharply decreased using this power generating system.

These features include: (a) the anode current circuit includes low minimum output in the range of 50-70 watts of microwave power, anode current stabilization in the range of ±0.5%, slow and soft anode current start with anode peak which is no more than 50% RMS and a soft magnetron shutdown with the anode peak no more than 50% RMS; (b) the filament current circuit includes a slow and soft start of a filament current, and soft filament shut down and a stable and wide-range automatic control for a filament current, which is based on the anode current value; (c) a power supply output that is not dependent on a supply line of voltage value, or a line of voltage fluctuation; (d) a power supply output that is not dependent on the current magnetron conditions such as anode and a magnet temperature, microwave reflection ration, etc, and stays stable during the whole operation cycle; (e) a high speed shut down (time to respond is less then 1 second) during a bad magnetron start or a bad magnetron operation, which is defined as either a magnetron's fault (vacuum breakdown) or a short-circuit in the high-voltage line or an arc in high-voltage line; and (f) high speed shut down (time to respond may be less then 1 second) during a bad magnetron operation which is characterized by anode voltage lower than a pre-determined working minimum and anode current higher than a pre-determined working maximum, or anode voltage higher than a pre-determined maximum, or anode current higher than a pre-determined maximum.

Figure 3:
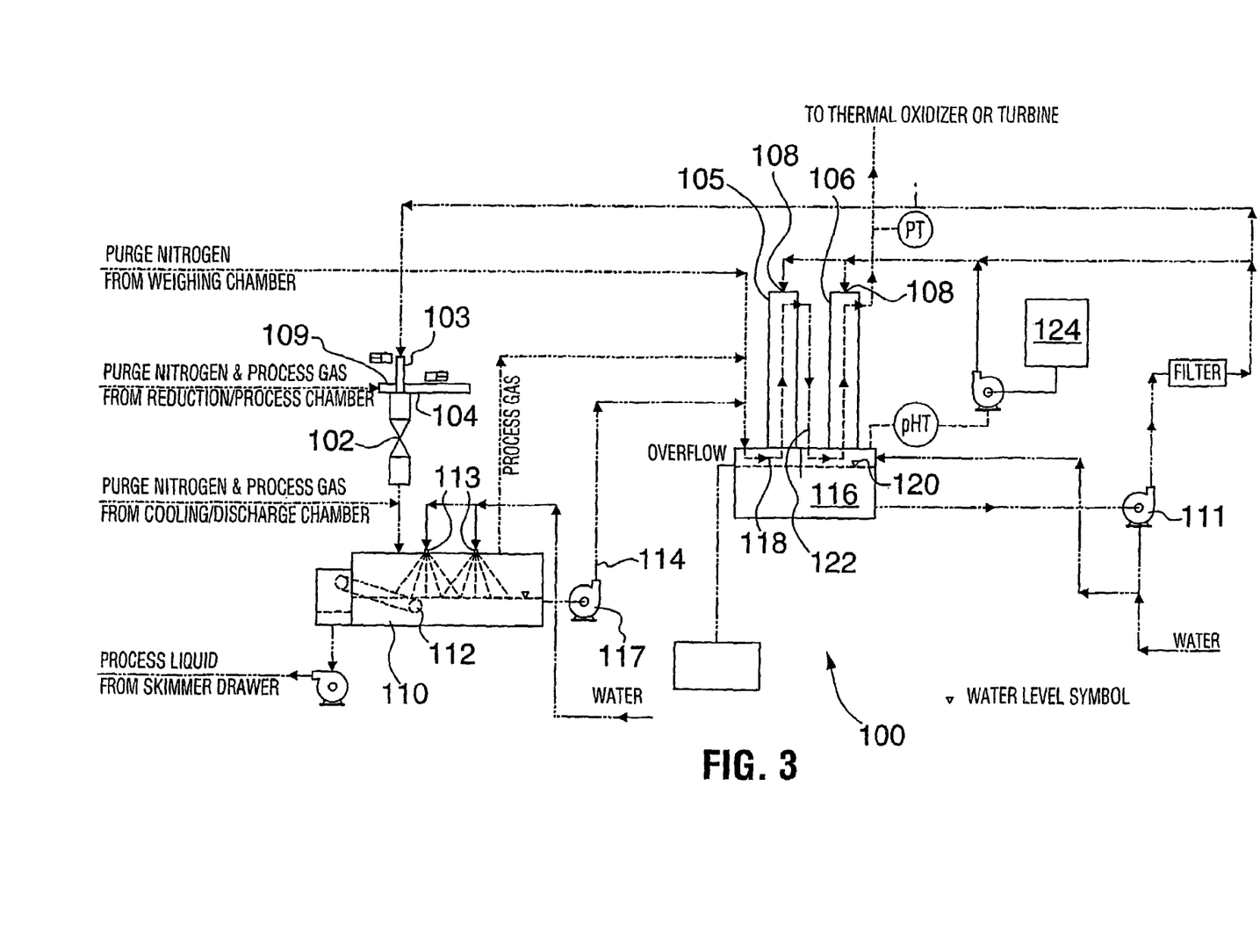
FIG. 3 is a schematic flow diagram of the environmental control system of the apparatus and process of the present invention.

During the reduction cycle all vapours that are generated from the treated waste are passed through the scrubber system 100. The scrubber system 100 is designed to remove hydrogen chloride, and hydrochloric acid from the gas stream, and to condense out any materials that have a liquid or solid phase below 100_C. The pH level of the scrubber water is controlled through the addition of sodium hydroxide.

The environmental control systems of the present invention are designed to deal with the process gas unique to the medical waste reduction system.

The scrubber system 100 consists of three contacting devices, a venturi 102 and two packed towers 104, 106. These devices remove Hydrochloric Acid (HCl) using Sodium Hydroxide (NaOH).

Pressure to operate the venturi 102 is provided by a submersible pump 111 that circulates the scrubber water through the venturi 102, and also through nozzles at 108 in the packed towers 105, 106.

The venturi 102 has a spray nozzle 103 located at the top of the venturi 102, which sprays water down through the venturi 102 creating a slight negative draw on the reduction chamber 12 and cooling the hot vapours as they enter the scrubber auxiliary tank 110, condensing any hydrocarbons that are not in gas phase at room temperature. This also provides a contacting surface for the process vapours. This contacting separates the "heavy hydrocarbons" from the rest of the process vapours. The spray nozzle's 103 position is pneumatically controlled allowing the small piece of vapour pipe 109 to be cleaned by a plunger 104 after each run. During a reduction run the nozzle 103 is in the down position, after the completion of a reduction run the nozzle 103 is moved to the upper location. When the nozzle 103 is in the upper position the plunger 104 extends and then retracts, the nozzle 103 then goes down for the next run. The plunger cleans the piece of pipe between the reduction chamber 12 and the venturi 102, depositing any buildup from the pipe into the reduction chamber 12. The buildup is processed with the next load. The whole process is controlled by the PLC.

The hydrocarbons are preferably collected using nozzles 113 to assist to direct the hydrocarbons to skimmer 112 and are stored until the next run. Once the next load of waste is in the reduction chamber 12, the collected hydrocarbons from the previous run are placed in the load and are further broken down in the reduction process.

The gas then flows through the auxiliary scrubber tank 110, and along a pipe 114 to the main scrubber tank 116, through the use of recirculating pump 117. The main scrubber tank 116 is separated into two compartments 118, 120, one for each of the packed towers 105, 106. The gas entering the first compartment 118 travels up the first tower 105 coming into contact with the water being sprayed from the top of the tower. The gas then exits the top of the first tower 105, and by means of piping 122, enters the second scrubber compartment 120. The gas then passes through the second tower 106, once again coming into contact with the water being sprayed from the top of the tower. The pH level is monitored in the main scrubber tank 116 and NaOH is added from source 124 as required to neutralize the HCl.

After the vapours exit the main scrubber tank 116, the vapours are further processed in a thermal oxidizer or turbine 125. The preferred process is a turbine where electricity can be generated, thus offering the total amount of electrical consumption for the process.

The design of the Plunger/Venturi has been found to be effective in eliminating the problem of clogged vapour pipes between the reduction chamber 12 and the auxiliary scrubber 110.

The scrubber system 100 also cleans the outlet gases from the first chamber 10, by direct venting into the main tank 116.

When the reduction cycle is completed the third shutter assembly 36 is opened and the reduced waste (composed mainly of sterile carbon residue) is transferred from the reduction chamber 12 to the cooling/grinding chamber 14. At any time after the reduction cycle is complete, the next waste load can be transferred into the weighing and purging chamber 10. As soon as shutter assembly 36 is closed and clamped, the next load can be transferred into the reduction chamber 12.

The temperature of the cooling chamber is monitored and once sufficient cooling has been achieved the waste will be fed by the conveyor 128, powered by motor 129 to a means of comminuting the treated and sterilized waste for ultimate disposal. That means for comminuting may be a shredder or grinder 130, or anything else suitable for reducing the treated and sterilized waste. The comminuted material is transferred by a pneumatic bulk transfer system, comprised of a blower 132, and cyclonic bag house 134. The reduced medical waste is discharged from the cyclone 134, through piping 136 into bags, or other bulk containers (not shown) for suitable disposal. Other material transfer systems could be used, depending upon customer requirements but typically, the amount of material at this point represents a reduction of approximately 70% mass and 90% volume of the material placed into the apparatus 2. There is also provided an access port 138 on each side of the chamber 14 to allow the operator to take samples of the processed material for testing or the like.

The shutter assemblies 18, 34 and 36 will now be discussed in greater detail with reference to FIGS. 5 to 8.

Each of the shutter assemblies perform the same function, namely to seal the chamber from the rest of the apparatus 2 and the environment.

Each of the shutter assemblies 18, 34 and 36 comprises a door 140 which is suspended on a door carrier frame 142 which in turn is guided on gibs 144. The door 140 is suspended to the frame 142 by horizontally arranged shoulder bolts 146 which allows a set amount of horizontal travel of the door 140 relative to the frame 142. Each suspension point at the shoulder bolts 146 is also provided with a helical compression spring 148, which pre-loads the door 140 and frame 142 in a position remote from the mating stationary door frame 150, i.e. the partially closed position. The door frame 142 carries seals 152, 154 are arranged in two parallel running grooves 156 which have a tapered cross-section (with trapezoidal shape) to maintain self-retention of the seals 152, 154. The seals 152, 154 may be high temperature gas seals made of silicone, or alternately microwave frequency seals made of woven monel mesh.

The vertical travel of the door 140 in each assembly 18, 34, 36 is provided by a master air driven cylinder 160 physically connected by a rod 162, or other suitable means to the door 140, such that when the cylinder 160 retracts, the door 140 is moved to the open position as shown.

Figure 8:
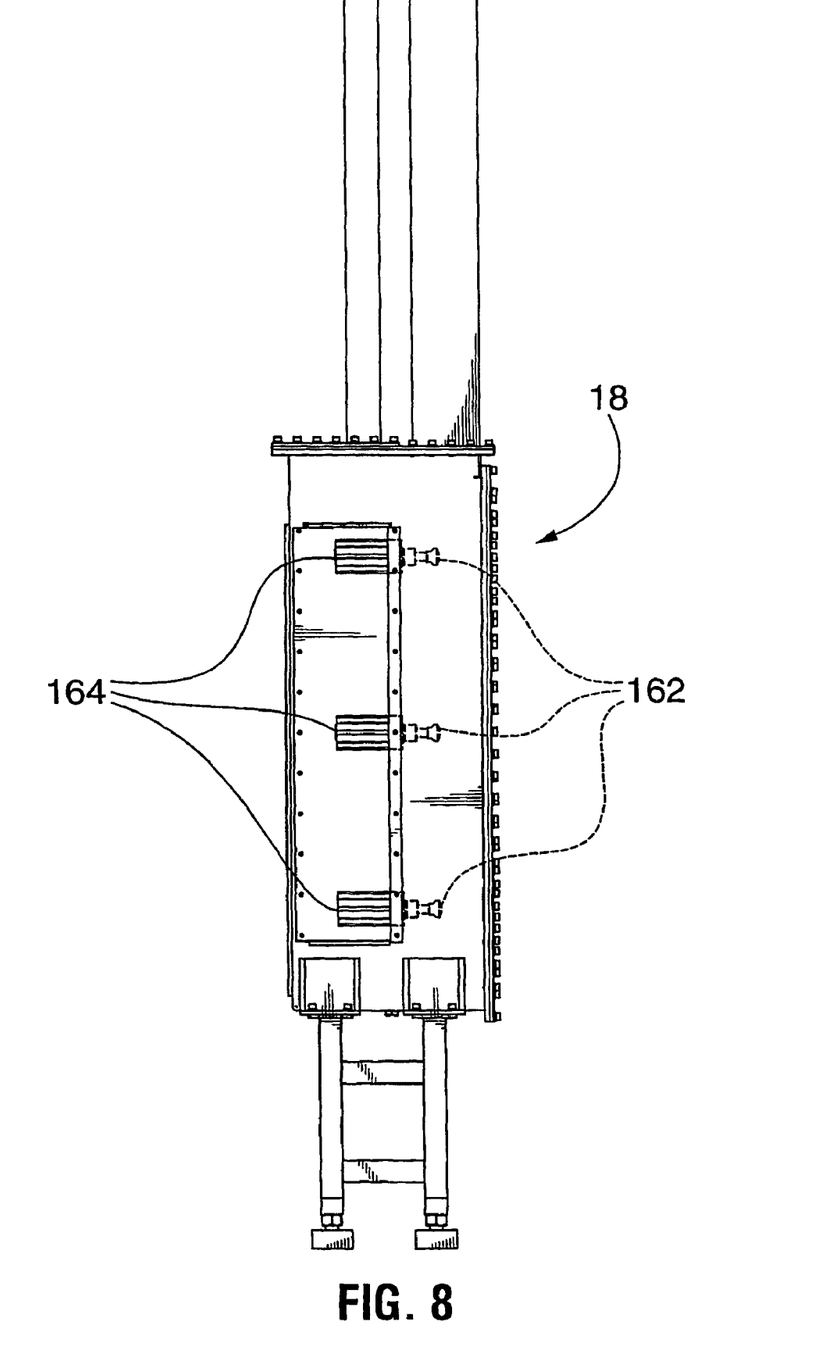
FIG. 8 is a side plan view of an alternate embodiment of a shutter assembly of the present invention.

The horizontal travel of the door 140 differs for the assembly 18 as compared with assemblies 34 and 36. For shutter 18, as shown in FIG. 8, the horizontal travel is controlled by a series of air cylinders 162 each operatively coupled to a camming assembly 164. The camming assembly 164 is constructed and oriented so as to exert a force against the door 140 when actuated by the cylinders 162.

Figure 5:
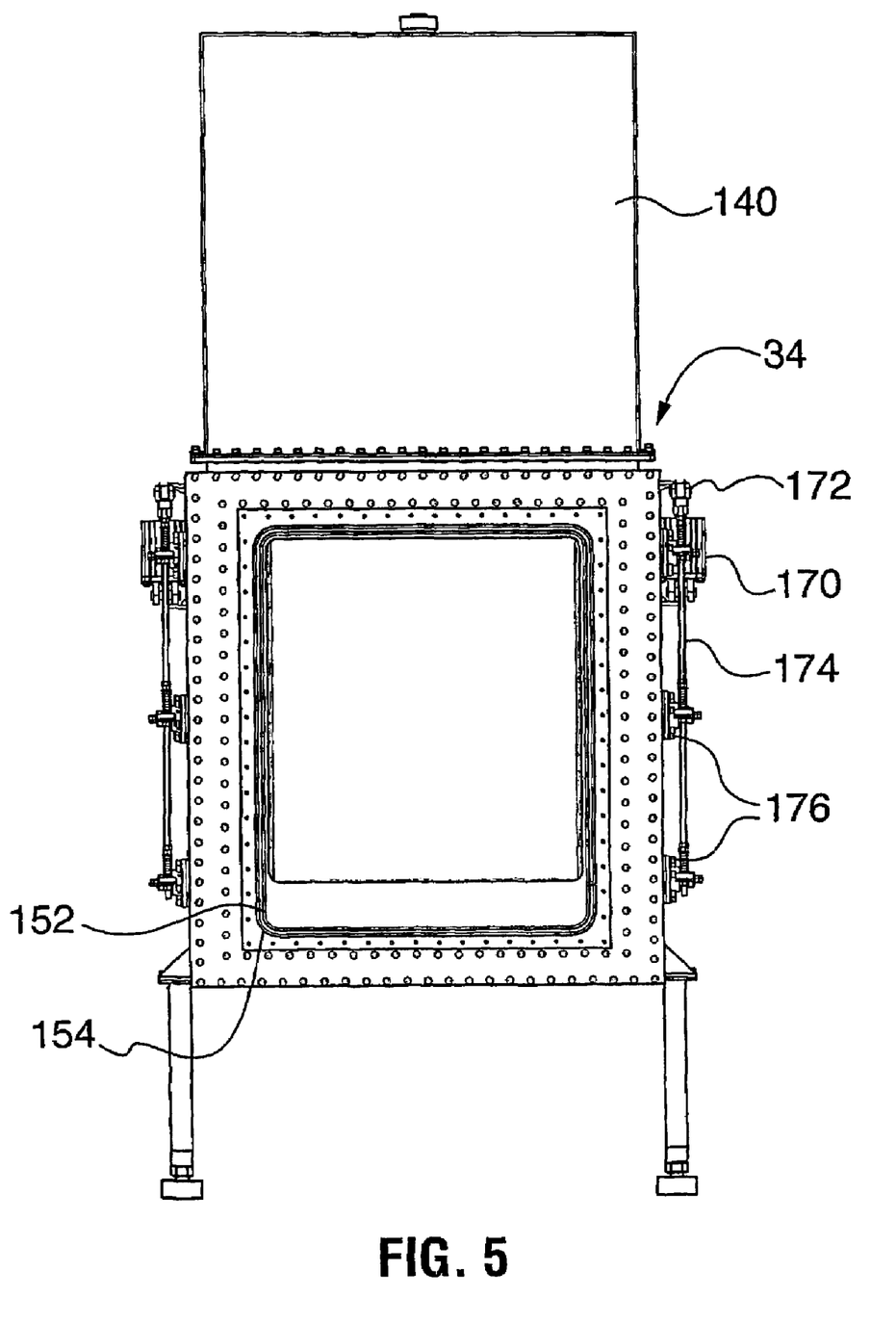
FIG. 5 is a front elevation view of an embodiment of a shutter assembly of the present invention.
Figure 6:
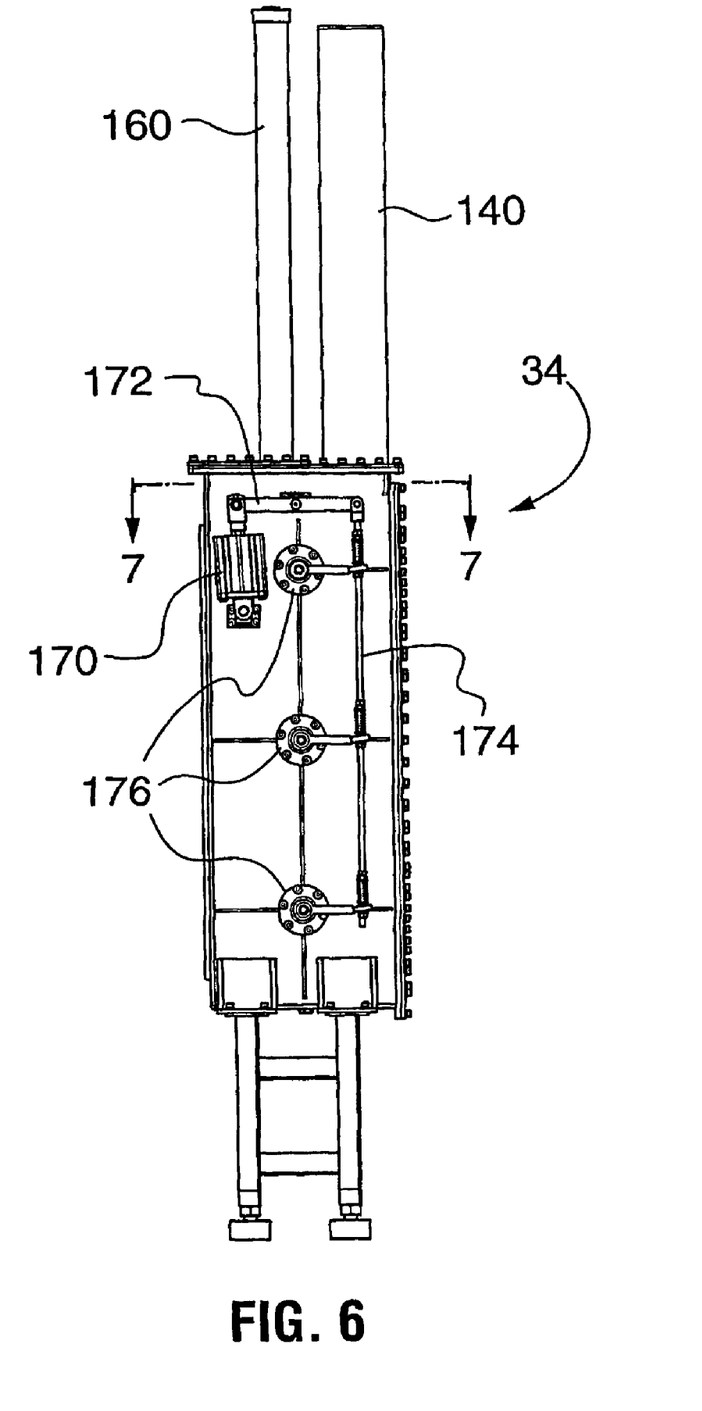
FIG. 6 is a side plan view of the embodiment of the shutter assembly shown in FIG. 5.
Figure 7:
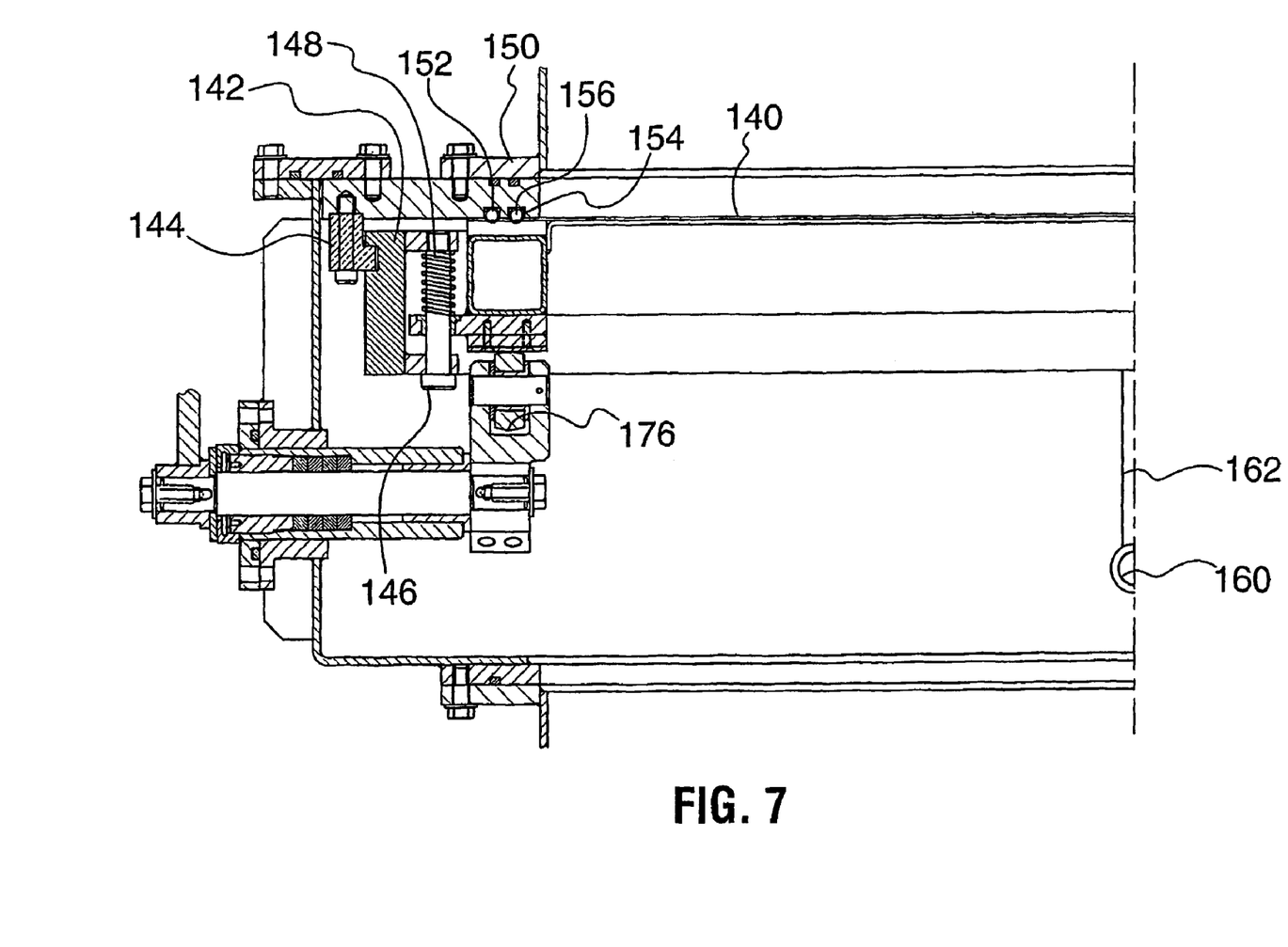
FIG. 7 is a cross-section view taken along line 7-7 of FIG. 6.

The horizontal travel of the door 140 in assemblies 34, 36 is controlled by a master cylinder 170 on each side of the door 140. The master cylinders 170 are coupled to a lever arm 172, which is in turn coupled, at its opposite end, to an actuator threaded rod 174. The rod 174 is in turn coupled to three camming arm assemblies 176 which move the door 140 in the horizontal direction between the partially closed and closed positions.

FIG. 7 shows the assembly 18 in cross-section. In the closed and sealed position, there is a constant pressure to push the door 140 against the seals 152, 154. Thus, any momentary change, caused by differential thermal expansions, changes in the door 140 or door frame 142 shape, etc., are instantaneously corrected by the continuously applied cam pressure, in a sort of live clamping manner.

Shutter assembly 36 is the mirror image in orientation to shutter assembly 34, so that the reduction chamber 12 can be sealed at both ends thereof. Thus, for both shutter assemblies 34, 36, the direction of travel of the door 140 to the closed position is toward the reduction chamber 12. The principle difference between shutter assembly 34 and shutter assembly 38 is that the discharge conveyor 128 enters shutter assembly 36. An access plate 180 is provided to access the conveyor 128, within shutter assembly 36 if needed.

Figure 9:
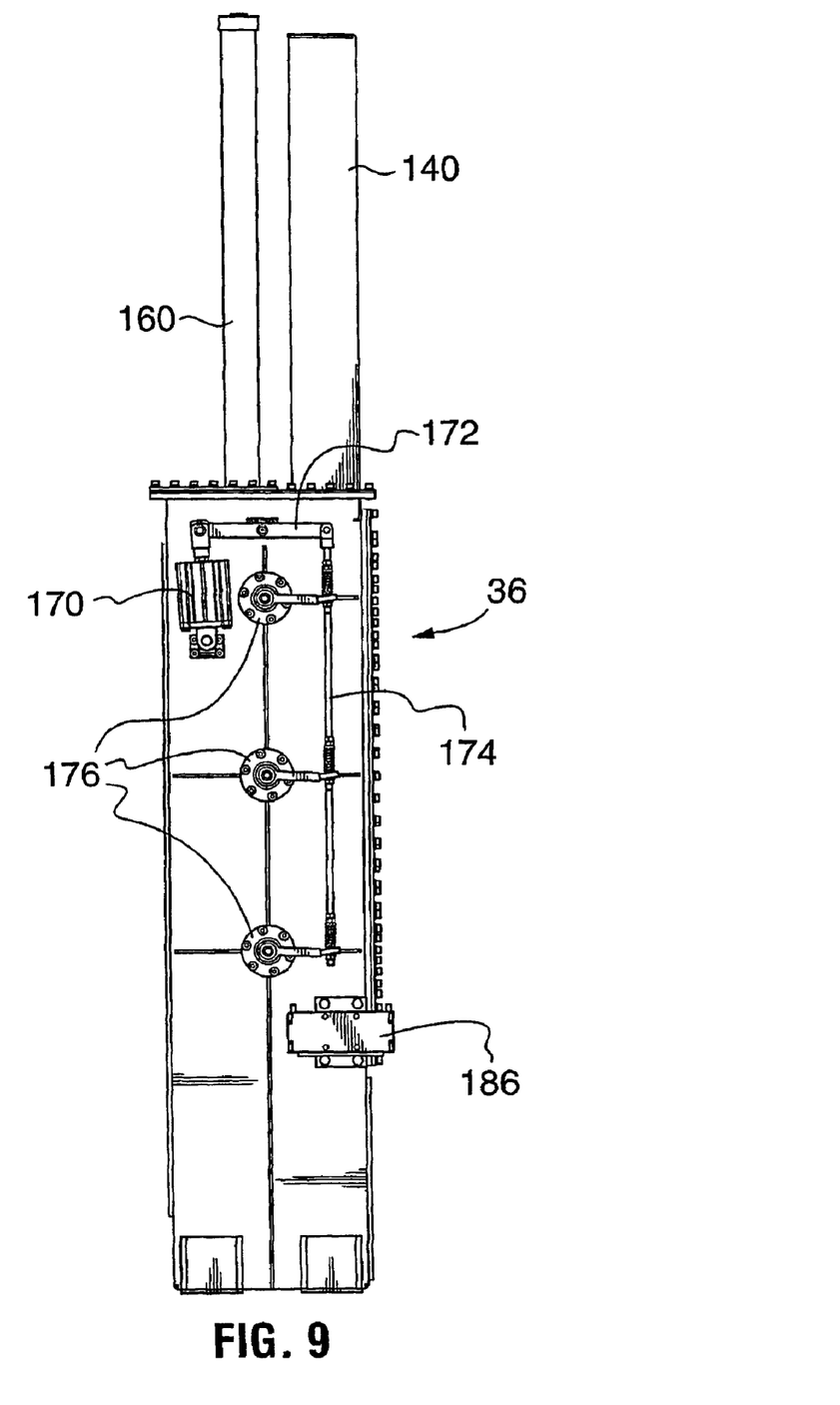
FIG. 9 is a side plan view of a further alternate embodiment of a shutter assembly of the present invention.

Both shutter assemblies 34 and 36 have a seal guard. Within shutter assembly 36, the seal guard 182 can be controlled by a cylinder 184 (as shown in FIG. 1) or a rotary actuator 186 (as shown in FIG. 9).

Thus, in use, the shutter assembly 34 will control the movement of the door 140 from the open position, vertically through to the partially closed position. During this movement, the spring 148 biases the door 140 and frame 142 away from the frame 150. Only when the door has reached the lowermost vertical position, the partially closed position, will the air cylinders 170 actuate the horizontal movement of the door 140 against the biasing force of the spring 148. During horizontal movement, the door 140 is prevented from vertical travel by means of interlocks (not shown).

Thus, it is apparent that there has been provided in accordance with the invention a medical waste unit, suitable for a process for uses in the reduction of organic waste that fully satisfies the objects, aims and advantages set forth above. While the invention has been described in conjunction with illustrated embodiments thereof, it is evident that many alternatives, modifications and variations will be apparent to those skilled in the art in light of the foregoing description. Accordingly, it is intended to embrace all such alternative, modifications and variations as fall within the broad scope of the invention.

We claim:

1. A process for the reduction of organic waste in an apparatus comprising a first chamber, a second chamber and a third chamber, the process comprising the steps of: loading said waste into said first chamber; weighing said waste; purging said first chamber of oxygen; transferring said waste to said second chamber; treating, sterilizing and reducing said waste for a first period of time by means of reverse polymerization using a reduction means comprising a plurality of magnetron assemblies for the application of microwave energy to said waste to treat, reduce and sterilize said waste, comprising a magnetron mounted on a waveguide and a porous, microwave transparent plate between said magnetron and said second chamber, said first period of time being determined by the weight of said waste determined by said weighing step; transferring said reduced waste to said third chamber; cooling said reduced waste for a second period of time; and comminuting said reduced waste for storage and ultimate disposal, wherein during the step carried out in each of said chambers, said chamber is sealed from the exterior of said apparatus, and from said other chambers.

2. The process of claim 1 wherein said purging step comprises the feed of nitrogen gas into said first chamber.

3. The process of claim 1 wherein said reverse polymerization is carried out by means of the non-pyrolytic application of microwave energy in an oxygen free atmosphere.

4. The process of claim 1 including the step of balancing the pressure in said first, second and third chambers such that the pressure in said first chamber and the pressure in said third chamber are maintained at a higher level than the pressure in said second chamber.

5. The process of claim 1 including the venting of gases generated by said treating, sterilizing and reducing step through at least one scrubber system to remove hydrogen chloride and hydrochloric acid from said apparatus.

6. The process of claim 5 wherein produced vapours are further treated by means of a thermal oxidizer or a turbine.

7. The process of claim 1 wherein said waste is moved throughout said apparatus by means of at least one conveyor.

8. An apparatus for the reduction of organic waste, the apparatus comprising: conveyor means to move said waste within said apparatus a first chamber comprising weighing means to determine a weight of said waste and purging means to purge said apparatus of oxygen; a second chamber comprising reduction means to treat, sterilize and reduce said waste for a first period of time, said first period of time being determined by the weight of said waste determined by said weighing means, said reduction means comprising a plurality of magnetron assemblies for the application of microwave energy to said waste to treat, reduce and sterilize said waste by means of reverse polymerization comprising a magnetron mounted on a waveguide and a porous, microwave transparent plate between said magnetron and said second chamber; a third chamber comprising cooling means to cool said reduced waste for a second period of time, comminuting means for comminuting said reduced waste for storage in storage means and ultimate disposal; and sealing means to seal each of said first, second and third chambers from the other chambers and from exterior of said apparatus when in use.

9. The apparatus of claim 8 wherein said comminuting means is selected from the group consisting of a grinder and a shredder.

10. The apparatus of claim 8 wherein said sealing means comprises a shutter assembly moveable between an open position and a partially closed position and between said partially closed position and a closed position.

11. The apparatus of claim 8 wherein said sealing means comprises a plurality of high temperature seals.

12. The apparatus of claim 11 wherein said seals are chosen from the group consisting of a high temperature gas seal and a high temperature microwave frequency seal.

13. The sealing device of claim 8 wherein said shutter assembly comprises: a door; a door frame, said door suspended on said door frame; drive means to move said door vertically between said open position and said partially closed position; and a cylinder assembly for moving said door horizontally between said partially closed position and said closed position.

14. The apparatus of claim 13 wherein said cylinder assembly comprises an air driven cylinder connected to one end of a lever, a threaded rod connected to an opposite end of said lever and at least one camming means rotatably connected to the rod, along its length, said camming means constructed so as to exert a force against said door when said lever and said rod are moved by said cylinder.

15. The apparatus of claim 13 wherein said cylinder assembly at least one coupling of a cylinder and a camming assembly, said camming assembly constructed so as to exert a force against said door when said cylinder is actuated.

16. The apparatus of claim 13 further comprising biasing means constructed so as to bias said door in said partially closed position when said door in at a lowermost vertical position.

17. The apparatus of claim 8 wherein said weighing means comprises load cells positioned around said conveyor means within said first chamber.

18. The apparatus of claim 8 wherein said purging means comprises a feed of nitrogen gas into said first chamber so as to displace any oxygen within said first chamber to prevent oxidation of said waste.

19. The apparatus of claim 8 further comprising at least one scrubber system for the venting of gas from said first chamber.

20. The apparatus of claim 8 constructed so that said first chamber and said third chamber are each maintained at a higher pressure than the pressure in said second chamber.

21. The apparatus of claim 20 wherein the pressure in said first and third chamber is about 0.1 to 0.5 psi higher than the pressure in said second chamber.

22. The apparatus of claim 8 further comprising at least one scrubber system for the venting of gases generated in said second chamber.

23. The apparatus of claim 22 wherein said scrubber system is constructed so as to minimize the escape of hydrochloric acid from said apparatus.

24. The apparatus of claim 8 wherein said magnetron assembly comprises a magnetron mounted on a side of a short rectangular waveguide, a flared end part mounted to an end of said waveguide, wherein the base of said end part is at or near said second chamber.

25. The apparatus of claim 24 further comprising a porous, microwave transparent plate between said magnetron and said chamber.

26. The apparatus of claim 8 further comprising a control system to monitor each stage of operation of said apparatus.

27. The apparatus of claim 8 wherein said drive means comprises an air cylinder operationally coupled to said door to raise and lower said door.

28. The apparatus of claim 27 further comprising limiting means to control the uppermost and lowermost positions of vertical travel of said door.

29. The apparatus of claim 8 further comprising a means for carrying said waste on said conveyor.

30. The apparatus of claim 29 wherein said means comprises a cardboard tray.

31. In an apparatus for the non-pyrolytic reduction of organic waste wherein said apparatus comprises a first chamber for weighing said waste, said first chamber purged of oxygen, a second chamber for treating, sterilizing and reducing said waste and a third chamber for cooling and comminuting said reduced waste, at least one sealing device comprising a shutter assembly moveable between an open position and a partially closed position and between said partially closed position and a closed position to seal each of said first, second and third chambers from the other chambers and from exterior of said apparatus when in said closed position.

32. The sealing device of claim 31 including a plurality of high temperature seals.

33. The sealing device of claim 32 wherein said seals comprise a high temperature gas seal and a high temperature radio frequency seal.

34. The sealing device of claim 31 wherein said shutter assembly comprises: a door; a door frame, said door suspended on said door frame; drive means to move said door vertically between said open position and said partially closed position; and at least one cylinder assembly for moving said door horizontally between said partially closed position and said closed position.

35. The sealing device of claim 34 further comprising biasing means constructed so as to bias said door in said partially closed position when said door in at a lowermost vertical position.

36. The apparatus of claim 34 wherein said cylinder assembly comprises an air driven cylinder connected to one end of a lever, a threaded rod connected to an opposite end of said lever and at least one camming means rotatably connected to the rod, along its length, said camming means constructed so as to exert a force against said door when said lever and said rod are moved by said cylinder.

37. In an apparatus for the reduction of organic waste wherein said apparatus comprises a first chamber, a second chamber and a third chamber, a plurality of magnetron assemblies for the application of microwave energy to said waste to treat, reduce and sterilize said waste by means of reverse polymerization in said second chamber, said magnetron assembly comprising a magnetron mounted on and with its anode projecting into a waveguide, means for isolating said magnetron from said second chamber comprising a porous, substantially microwave transparent plate mounted adjacent an end of said waveguide, and tuning means in said waveguide for optimizing coupling of said magnetron to said chamber wherein an end part of said waveguide adjacent said second chamber comprises a truncated cone.

38. The magnetron assembly of claim 37 wherein the length of said waveguide is limited to substantially that required to allow mounting of said magnetron on a side thereof.

39. The magnetron assembly of claim 37 including means for introducing a coolant to said waveguide for cooing said anode.

40. The magnetron assembly of claim 37 wherein said plate is mounted adjacent a narrower end of said flared end part.

* * * * *